United States Patent [19]

Scaife

[11] 4,052,986
[45] Oct. 11, 1977

[54] DEVICE FOR INTRODUCING MEDICAMENTS OR THE LIKE INTO BODY CAVITIES

[75] Inventor: Colin Scaife, Cottingham, England

[73] Assignee: Reckitt & Colman Products Limited, London, England

[21] Appl. No.: 615,104

[22] Filed: Sept. 19, 1975

[30] Foreign Application Priority Data

Oct. 9, 1974 United Kingdom ............... 43787/74
Feb. 6, 1975 United Kingdom ................ 5183/75

[51] Int. Cl.² ...................... G61M 3/00; B65D 35/20
[52] U.S. Cl. ..................................... 128/260; 128/232; 128/248; 128/251; 128/272; 222/190; 222/541
[58] Field of Search ........... 128/260, 261, 231, 214 R, 128/232 R, 251, 272, 272.1, 272.3, 274, 248; 222/80, 212, 215, 541, 95, 190

[56] References Cited

U.S. PATENT DOCUMENTS

| 39,662 | 8/1863 | Lockwood | 128/231 |
| 94,620 | 7/1969 | Lockwood | 128/231 |
| 1,507,498 | 9/1924 | Matthews | 128/231 X |
| 1,940,122 | 12/1933 | Gardner | 128/231 |
| 2,180,063 | 11/1939 | McKinley | 128/231 |
| 2,864,367 | 12/1958 | Mende | 128/261 |
| 2,876,935 | 3/1959 | Lindberg | 222/145 |
| 3,010,613 | 11/1961 | Stossel | 222/190 |
| 3,204,835 | 9/1965 | Michel | 222/541 |
| 3,225,970 | 12/1965 | Rooney | 222/484 |
| 3,339,812 | 9/1967 | Meissner | 222/566 |
| 3,461,868 | 8/1969 | Palich | 222/215 X |
| 3,938,706 | 2/1976 | Cohen | 222/95 |

FOREIGN PATENT DOCUMENTS 1,041,548 9/1966 United Kingdom ................ 128/272

Primary Examiner—Aldrich F. Medbery
Attorney, Agent, or Firm—Bacon & Thomas

[57] ABSTRACT

A device for introducing aqueous compositions, especially those containing medicaments, in the form of a foam to a body cavity such as the colon or vagina, comprising a plastic container having a resilient deformable body portion, a dispersing end adapted to engage with the opening of the body cavity and a second end adapted to engage with a one-way valve assembly. When the container is partially filled with a foamable composition and a one-way valve assembly is attached foam may be expelled from the dispensing end into the body opening by squeezing the container body and on releasing the squeezing action air enters through the one-way valve assembly so that the container resumes its original shape ready for a further cycle of squeezing and reinflation.

7 Claims, 7 Drawing Figures

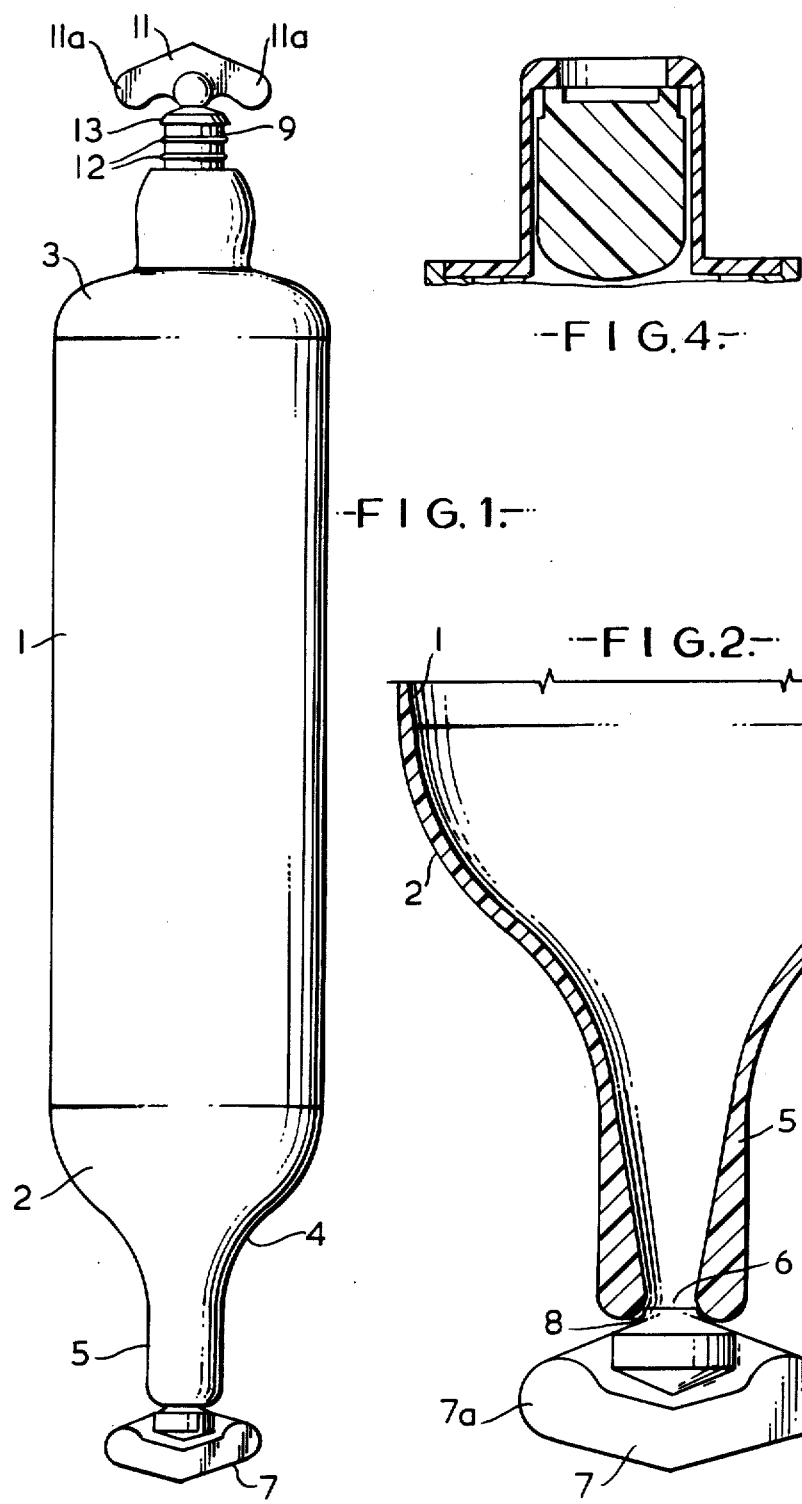

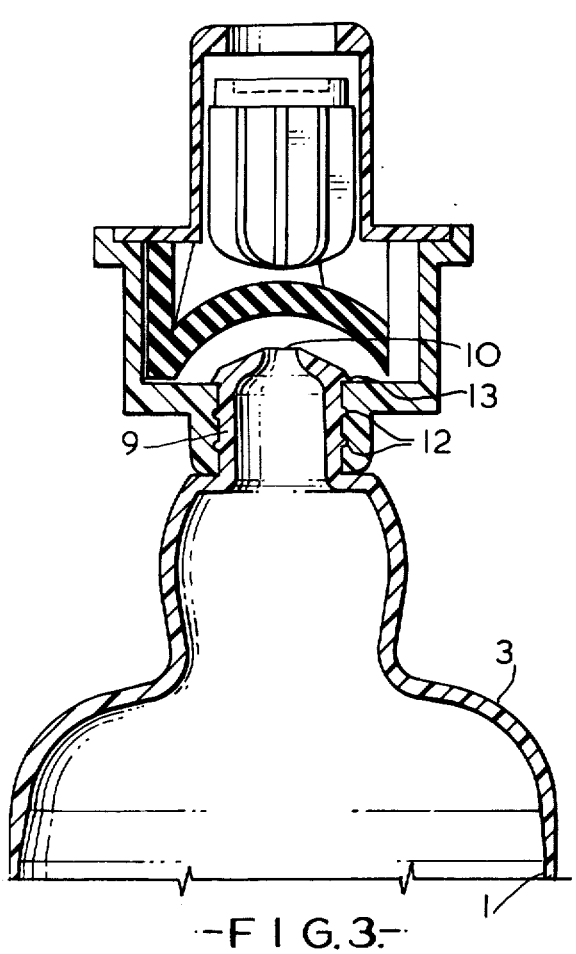
-FIG.3.-
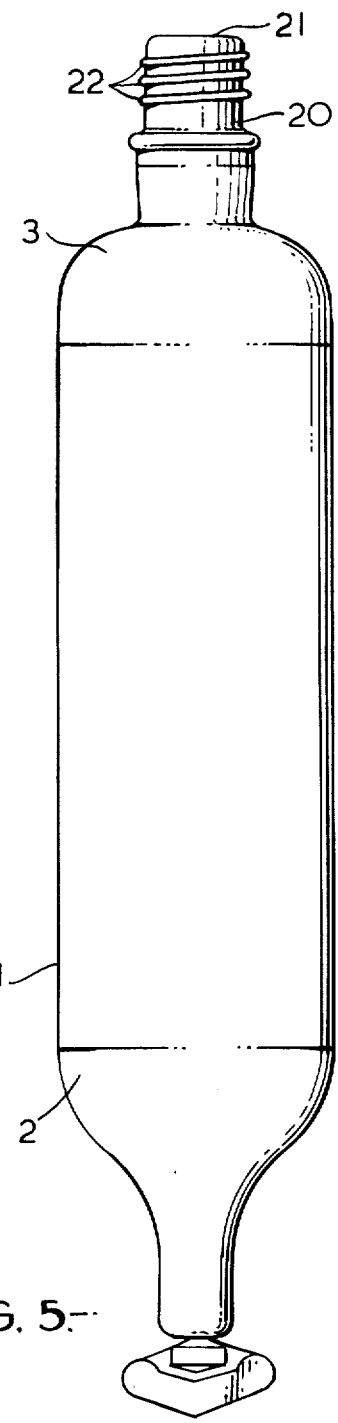
-FIG.5.-

DEVICE FOR INTRODUCING MEDICAMENTS OR THE LIKE INTO BODY CAVITIES

This invention relates to a device for introducing a medicinal medium to a body cavity and in particular to a device by means of which a medicinal medium in the form of a foam may be applied.

Medicaments to be applied to the colon are normally administered via the rectum or a colostomy stoma in the form of a suppository or an enema. However such medicaments administered via a suppository tend only to reach, and be absorbed through, the terminal colon, and thus this method is unsatisfactory when it is desirable for the medicament to penetrate further up the colon. With enemas the medicament tends to penetrate further up the colon, the distance of course being dependent upon the volume of liquid employed. In adults the colon is about 1.5 m long with a capacity of nearly 2½ liters, and consequently a considerable volume of liquid is required to fill the colon completely, and even only to fill the distal part requires a large volume of liquid. There are two main types of enema namely those that are administered by gravity feed via a cannula employing large volumes of fluid and those which are disposable and employ rather smaller volumes of fluid. In order to stimulate peristalsis of the colon with the former 1-1½ pints of soft green soap solution (5%) are commonly employed whereas with the latter a single dose disposable enema comprising a plastic bag with a rectal tube containing 100 to 150 ml of solution of for example Arachis oil, magnesium sulphate or sodium phosphate is employed. Clearly with either type of enema when it is necessary for the medicament to penetrate further up the colon greater volumes of liquid are required.

According to this invention there is provided a device for introducing an aqueous composition in the form of a foam into a body cavity comprising a plastic container having a deformable resilient body portion, a dispensing end adapted to engage with the opening to the body cavity with a normally closed discharge aperture, and a second end adapted to engage with a one-way valve assembly and having a normally closed air-inlet.

Such devices are particularly suited for administering medicinal media in the form of a foam to the vagina or the colon through the anus or a colostomy stoma.

Suitable plastics from which the device may be formed include high density polyethylene, polypropylene, polyvinylchloride, copolymer of ethylene with up to 12% vinyl acetate, and preferably low density polyethylene. Conveniently the body portion is of a plain or fluted cylindrical shape which is deformable on the application of exterior pressure i.e. by squeezing, and resilient so that it restores to its original shape after deformation. Preferably the two ends are more rigid than the body portion.

A closure for the normally closed discharge aperture may take the form of a positionable and removable plug or cap. Preferably, however, as a means of maintaining a high level of sterility within the container the closure for the discharge aperture may be initially integral therewith being separable immediately prior to use to expose the discharge aperture. Most conveniently the closure is formed integral with the container being separable at a zone of weakness having a reduced wall thickness and is further formed with an extended portion, such as a wing-like member by means of which the closure may be grasped by the fingers to effect separation as for example, by twisting action to expose the discharge aperture. A closure for the normally closed air-inlet may be constructed in like manner or may be formed of a frangible diaphragm.

The one-way valve assembly which when attached to the device is to permit ingress of air but minimise egress of the container contents may be of plastics material such as polystyrene. It may be attachable to the device as a push-on fit or preferably with a screw threaded portion for engagement with a complementary portion on the device.

In another aspect of the invention there is provided a device for introducing an aqueous composition having a deformable resilient body portion, a dispensing end adapted to engage with the opening to the body cavity with a normally closed discharge aperture, and a second end engaging with a one-way valve assembly and having a normally closed air-inlet.

In order to use the device to introduce an aqueous composition in the form of a foam to a body cavity the device before sealing is partially filled (about a quarter full) with an aqueous composition comprising for example a medicament or an X-ray contrast media, a foaming agent and a foam stabiliser.

In a further aspect of the invention there is provided a device for introducing an aqueous composition in the form of a foam into a body cavity which device comprises a plastic container which has a deformable resilient body portion, a dispensing end adapted to engage with the opening to the body cavity with a normally closed discharge aperture, and a second end adapted to engage with a one-way valve assembly having a normally closed air inlet, said container containing an aqueous foamable composition comprising a medicament or X-ray contrast media, a foaming agent and a foam stabiliser.

Embodiments of the invention are by way of example hereinafter described and illustrated in the accompanying drawing in which:

FIG. 1 is a side view of a device for introducing a medicinal medium in the form of a foam to a colostomy stoma and being adapted to engage with a push-on one-way valve assembly.

FIG. 2 in an enlarged fragment of the device of FIG. 1 showing the variation in the wall thickness to achieve suitable rigidity of the discharge end and resilience of the main body portion of the device.

FIG. 3 is an enlarged fragment of the device of FIG. 1 showing the air-inlet and one-way valve assembly attached with the valve being shown in the open position.

FIG. 4 is a partial section of the one-way valve assembly of FIG. 3 with the valve being shown in the closed position.

FIG. 5 is a side view of a second device for use with a colostomy stoma and being adapted to engage with a screw-on one-way valve assembly.

Figure 6:
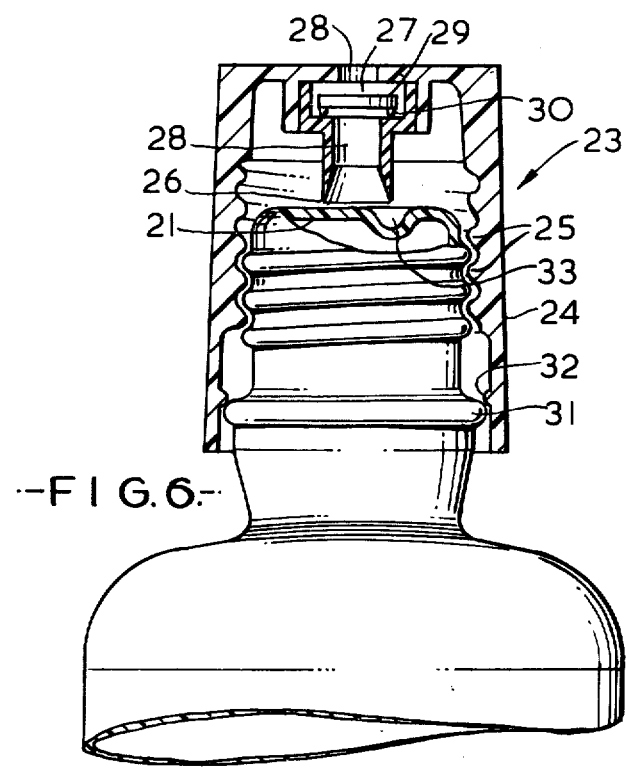
FIG. 6 is an enlarged fragment of the second device showing the valve assembly attached but with the air-inlet closure intact.

Referring now to FIGS. 1 to 4 of the drawings the device comprises a preferably elongate container moulded from low density polyethylene or similar plastics material such as an ethylene/vinyl acetate copolymer, with a deformable resilient cylindrical central body portion 1 and ends 2 and 3, the thickness of the walls of the ends being greater than that of the central body portion and therefore imparting a great degree of shape retention. The discharge end 2 has a shoulder portion 4 so shaped as to make good sealing contact when the device is applied to a colostomy stoma, and a neck 5 defining a discharge passageway terminating in a discharge aperture 6 closed by an closure 7 of one piece with the container wall and attached to the neck 5 by a peripheral zone of weakness having a reduced wall thickness 8. The closure 7 is provided with means, conveniently in the form of wings 7a, by means of which the closure may be gripped and twisted to rupture and said zone of weakness. The second end 3 has a neck 9 defining an air-inlet passageway terminating in an air-inlet aperture 10 closed by a closure 11 of one piece with the container wall and attached to the neck 9 by a peripheral zone of weakness having a reduced wall thickness. Again said closure 11 is provided with means, conveniently in the form of wings 11a, by means of which the closure may be gripped and twisted to rupture said zone of weakness.

In order to be able to attach a push-on one-way valve assembly (after twisting off the closure 11 as explained) the neck 9 is formed with two sealing rings 12 in the form of annular projections and an annular retaining ring 13 which afford sealing contact and retaining means for a push-on one-way valve assembly such as that illustrated in FIGS. 3 and 4 marketed by N. R. Fitments Limited and as described in the specification of British pat. specification No. 835,507.

The device may be moulded, partially filled with an aqueous composition, and hermetically sealed in a single machine such as a form-fill-seal-machine of the type described in the specification of British patent specification No. 1,041,548, conveniently under aseptic conditions.

For the purpose of introducing a foamed enema to a colostomy stoma a suitable sized container is one having an internal capacity of about 200 mls and containing some 30 to 50 mls of an aqueous foamable composition.

In operation the device is shaken to generate foam, the closure 11 is twisted off as described above and the one-way valve assembly connected. The closure 7 is then twisted off as described above leaving any residual sharp edge from the peripheral zone of weakness inside the neck 5 so that when the neck is then inserted into the stoma the colon lining is not damaged. The body portion is squeezed to expel foam into the colon, the one-way valve assembly serving to minimise egress of foam through the air-inlet aperture. Upon completion of the squeezing action, whilst maintaining the device pressed against the stoma, the resilient walls of the container commence to return to their original undeformed shape, so creating a partial vacuum within the device which causes the one-way valve to open and allow air to enter. The cycle of squeezing and reinflation is repeated until an adequate amount of foam has been expelled. To aid penetration of the foam further up the colon the cycle can be further repeated so that mainly air is blown into the colon.

Figure 7:
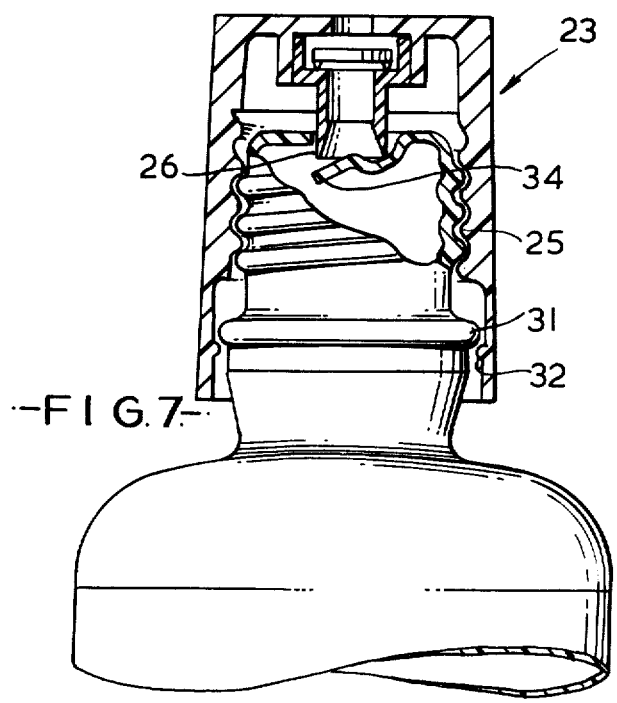
FIG. 7 is an enlarged fragment of the second device showing the valve assembly attached to the device with the air-inlet closure pierced.

Referring now to FIGS. 5 to 7 of the drawings a second embodiment is illustrated. The device shown in FIG. 5 differs only from that shown in FIG. 1 in respect of the contruction of the second end. The second end 3 has a neck 20 defining an opening closed by a frangible diaphragm 21, the neck having an externally threaded portion 22.

A valve assembly 23 is provided with a skirt 24 defining a recess having an internally threaded portion 25 for engagement with the threaded portion 22 of the neck of the device, the recess is also provided with a boss having a cutting edge 26 such that on the valve assembly being screwed down the neck of the container the cutting edge 26 pierces the frangible diaphragm 21. The valve assembly has above the recess a chamber 27, connected by channels 28 to the recess and to an air-inlet, and having a valve member 29 within the chamber. The valve member which is provided with studs 30 on its lower side is movable under the influence of varying air pressures on the upper and lower sides of said valve member between an open position (as shown in FIGS. 6 and 7) permitting ingress of air and in the closed position eliminating or minimising egress through the air-inlet. (In an alternative construction the lower side of the valve member 29 is flat and the lower surface of the chamber 27 is provided with studs against which the valve member abuts in the open position). Conveniently the members of the valve assembly are moulded of plastics, such as polystyrene.

In operation the device is shaken to generate foam, the valve assembly screwed down the neck of the device with the cutting edge piercing the frangible diaphragm, the closure 7 (see FIG. 2) twisted off, the subsequent procedures being as described above.

Conveniently the neck 20 of the device may be provided with an annular bead 31 and the valve assembly with an inwardly projecting ring 32 within the skirt, so that when the valve assembly is initially screwed onto the device the annular bead 31 abuts against the ring 32 with the cutting edge 26 spaced from the frangible diaphragm 21. The device may be packaged with the valve assembly screwed on in this manner. Further twisting of the valve assembly relative to the device drives the ring 32 past the annular bead 31, moving the cutting edge 26 toward the frangible diaphragm 21 to pierce the same.

The frangible diaphragm may be provided with a shallow depression 33 so that when the valve assembly is screwed down the neck of the container and the cutting edge 26 pierces the frangible diaphragm the base of the depression is not cut through and thus the resulting cut-away portion 34 of the diaphragm is less likely to fall into the device and so possibly block the discharge orifice 6 (see FIG. 2). Advantageously the discharge orifice 6 is smaller than the cut-away portion 34 so that should the latter be completely severed it should not pass through the discharge orifice into the body.

The two embodiments described and illustrated are for application to the colon via a colostomy stoma, however, for application to the anus the discharge end will be longer. It will be appreciated that such devices although primarily intended for human use may also be used with animals.

As stated an aqueous composition for use in the device may comprise a medicament or X-ray contrast media, a foaming agent and a foam stabiliser. To minimise possible irritation to the colon the compositions when intended to be applied to the colon are preferably buffered to about pH 7 by the incorporation of a suitable buffering system for example tris(hydroxymethyl)methylamine and sodium citrate.

For the purposes of assisting bowel evacuation the medicament will comprise at least one compound having a laxative effect such as for example dioctyl sodium sulphosuccinate, an alkali or alkaline earth metal phosphate, bisacodyl, oxyphenisation or an anthraquinone derivative.

As a treatment for ulcerative colitis the medicament will comprise at least one compound, such as corticosteriod, having anti-inflammatory activity, for example prednisolone, hydrocortisone or betamethasone or their esters or salts.

Other types of medicament that are conventionally administered via the colon are local anaesthetics for example lignocaine, sedatives for example chlorpromazine hydrochloride, bronchodilators for example aminophylline and analgesics for example pentazocine.

Suitable X-ray contrast media are barium sulphate and poly iodo-styrene resin.

It will be appreciated that the foaming agent should be selected from those soaps and detergents that are pharmaceutically acceptable when applied to a body cavity such as the colon or the vagina, examples of such materials being for example sodium lauryl sulphate and cetrimide. There are medicaments such as for example dioctyl sodium sulphosuccinate which also behave as foaming agents and in those cases it may not be necessary to have present an additional foming agent.

In order to maintain the foam when generated the composition includes a foam stabiliser such as for example coconut diethanolamide or hydroxypropylmethylcellulose.

Preferably the aqueous composition incorporates a preservative such as for example methyl or propyl p-hydroxy benzoate.

With this type of device delivering a medicament in the form of a foam a smaller volume of liquid is employed as compared with a conventinal enema, and as a consequence the frequency of premature leakage from the colon is much reduced. In addition the foam penetrates further up the colon.

The following are examples of formulations which may be applied to the colon employing the devices of the invention.

EXAMPLE 1

Laxative dioctyl sodium sulphosuccinate: 1.0 g
hydroxylpropylmethylcellulose: 1.3 g
methyl p-hydroxy benzoate: 0.15 g
water: to 100.00 ml

EXAMPLE 2

Buffered Laxative dioctyl sodium sulphosuccinate: 1.0 g
hydroxypropylmethylcellulose: 1.3 g
methyl p-hydroxy benzoate: 0.15 g
tris(hydroxymethyl)methylamine: 0.15 g
sodium citrate monohydrate: 0.08 g
water: to 100.00 ml

EXAMPLE 3

Ulcerative Colitis Formulation prednisolone sodium phosphate 0.054 g
incorporated into formulation of Example 2

EXAMPLE 4

X-Ray Contrast Media barium sulphate 60.0 g
incorporated into formulation of Example 2

What is claimed is:

1. An improved enema device of the type including a container having a resilient, deformable body portion defining an enclosed space, the improvement comprising:
   a. a first end having a first frangible closure, said first end having means for admitting air from the exterior of said body portion into said enclosed space and for restraining flow of container contents out of said enclosed space to the exterior of said body portion, said admitting and restraining means including a one-way air inlet valve;
   b. a second end having means for selectively providing, prior to use, an open dispensing applicator shaped for non-traumatic insertion into an orifice in a body cavity, said providing means including a second frangible closure for exposing said enclosed space;
   c. said second end also being shaped to make sealing contact with respect to the orifice in the body cavity.

2. An improved enema device as defined in claim 1, wherein said container is completely hermetically sealed and is defined by a one-piece container wall.

3. An improved enema device as defined in claim 1, wherein said container wall is thicker in the regions of said first and second ends than in the region of said body portion, whereby the regions of said ends are more rigid than the region of said body portion.

4. An improved enema device as defined in claim 1, wherein said valve is housed in a skirt, said skirt defining a recess with a boss disposed in said recess, said boss having a cutting edge thereon, said valve skirt being movable with respect to said container, whereby said boss may pierce said first frangible end.

5. A container for use in administering a foam enema, the container comprising:
   a. a wall defining a completely hermetically sealed container enclosing an interior space, said container including a resilient deformable body portion and being partially filled with a foamable substance;
   b. means for converting one end of said completely sealed container into and open dispensing applicator shaped for non-traumatic insertion into an orifice in a body cavity and for converting said container into a device by which foam may be continuously pumped from the container by repeated squeezing and release of the resilient deformable body portion, said converting means including one frangible portion at said one end of said container for providing access to said interior space and another frangible portion at said other end, said other end having a coupling for accepting a one-way air inlet valve;
   c. said one end being shaped to make sealing contact with respect to the orifice in the body cavity.

6. A container as defined in claim 5 wherein said hermetically sealed wall is of one piece.

7. A container as defined in claim 5, wherein said wall is thicker in the regions of said first and second ends than in the region of said body portion, whereby the regions of said ends are more rigid than the region of said body portion.

* * * * *